US012799223B2

(12) United States Patent
Zhang et al.

(10) Patent No.: US 12,799,223 B2
(45) Date of Patent: Nov. 17, 2026

(54) ANTI-CD73 MONOCLONAL ANTIBODIES

(71) Applicant: Northwestern University, Evanston, IL (US)

(72) Inventors: Bin Zhang, Evanston, IL (US); Siqi Chen, Evanston, IL (US); Jie Fan, Evanston, IL (US)

(73) Assignee: Northwester University, Evanston, IL (US)

( * ) Notice: Subject to any disclaimer, the term of this patent is extended or adjusted under 35 U.S.C. 154(b) by 662 days.

(21) Appl. No.: 18/546,905

(22) PCT Filed: Feb. 22, 2022

(86) PCT No.: PCT/US2022/017302

§ 371 (c)(1),
(2) Date: Aug. 17, 2023

(87) PCT Pub. No.: WO2022/178416

PCT Pub. Date: Aug. 25, 2022

(65) Prior Publication Data

US 2024/0124606 A1 Apr. 18, 2024

Related U.S. Application Data

(60) Provisional application No. 63/152,116, filed on Feb. 22, 2021.

(51) Int. Cl.

| | |
|---|---|
| ***A61K 39/395*** | (2006.01) |
| ***A61K 39/00*** | (2006.01) |
| ***A61P 35/00*** | (2006.01) |
| ***C07K 16/28*** | (2006.01) |
| ***C12N 15/63*** | (2006.01) |

(52) U.S. Cl.

CPC ...... *C07K 16/2896* (2013.01); *A61K 39/0011* (2013.01); *A61K 39/3955* (2013.01); *A61P 35/00* (2018.01); *C12N 15/63* (2013.01); *A61K 2039/5156* (2013.01); *C07K 2317/565* (2013.01); *C07K 2317/77* (2013.01)

(58) Field of Classification Search

CPC ........................ A61K 39/3955; C07K 16/2896
See application file for complete search history.

(56) References Cited

U.S. PATENT DOCUMENTS

| | | | | |
|---|---|---|---|---|
| 2019/0062456 | A1 * | 2/2019 | Lonberg | A61K 39/3955 |
| 2019/0256598 | A1 * | 8/2019 | Wang | A61K 35/17 |

* cited by examiner

*Primary Examiner* — Xiaozhen Xie
(74) *Attorney, Agent, or Firm* — Casimir Jones, S.C.; David W. Staple

(57) ABSTRACT

Provided herein are monoclonal antibodies (mAbs) that bind to human Cluster of Differentiation 73 (CD73). In particular, anti-CD73 mAbs are provided that bind to and inhibit the activity of human CD73.

14 Claims, 11 Drawing Sheets

Specification includes a Sequence Listing.

FIG. 1A-D
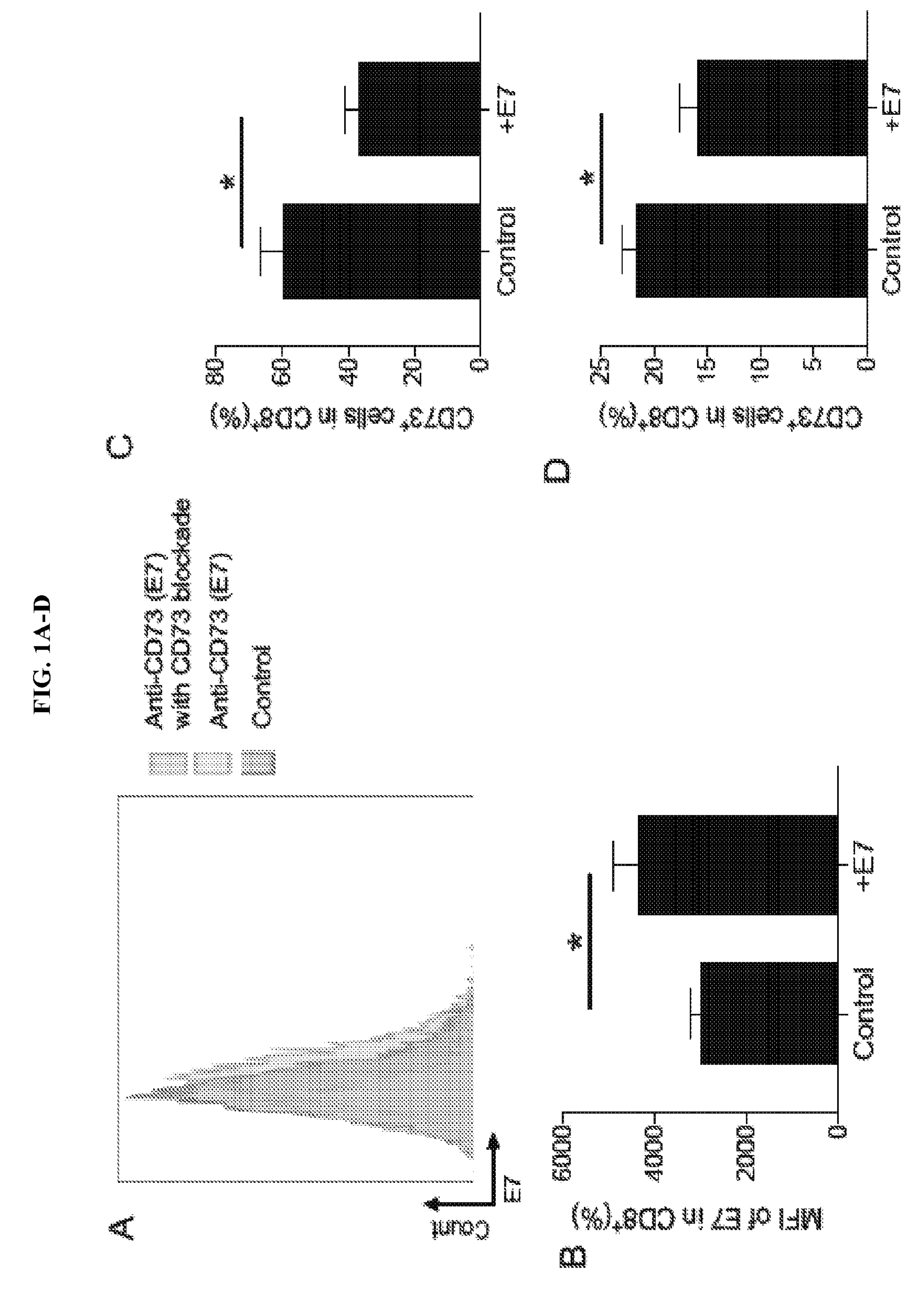

FIG. 2A
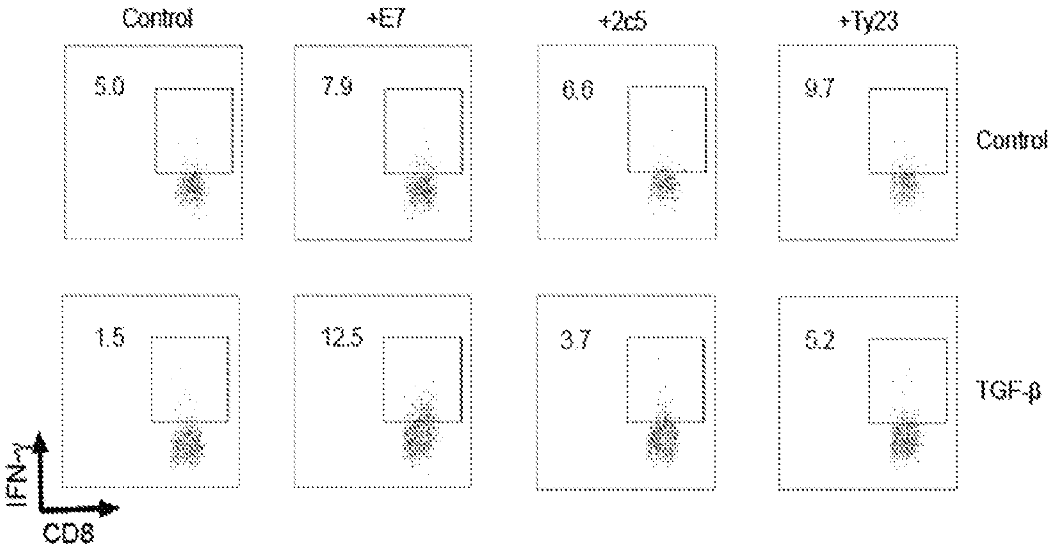
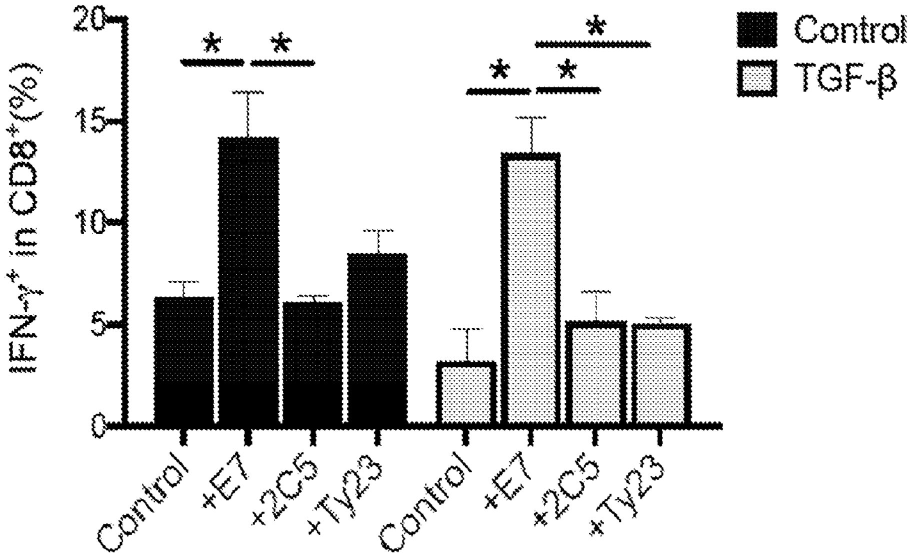
FIG. 2B

FIG. 2C
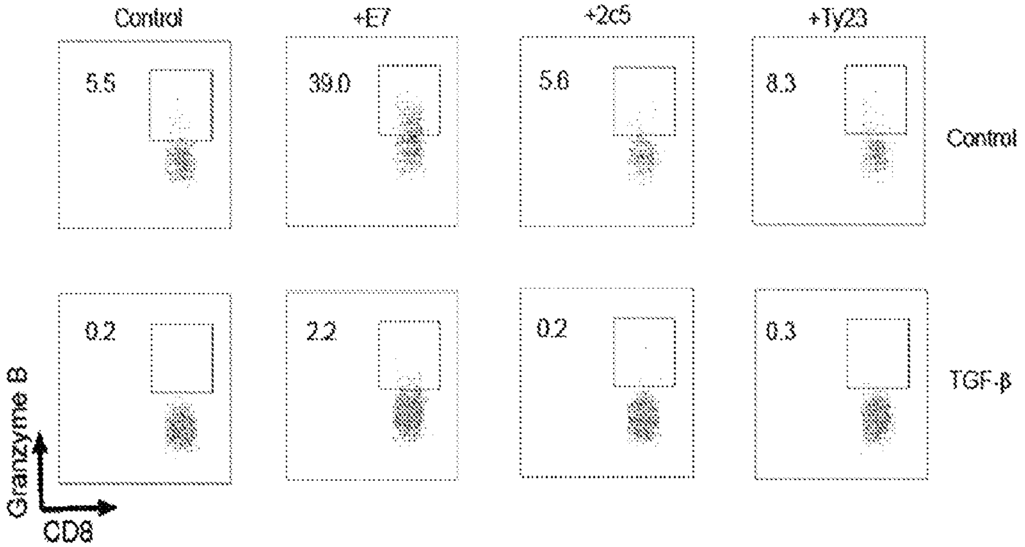
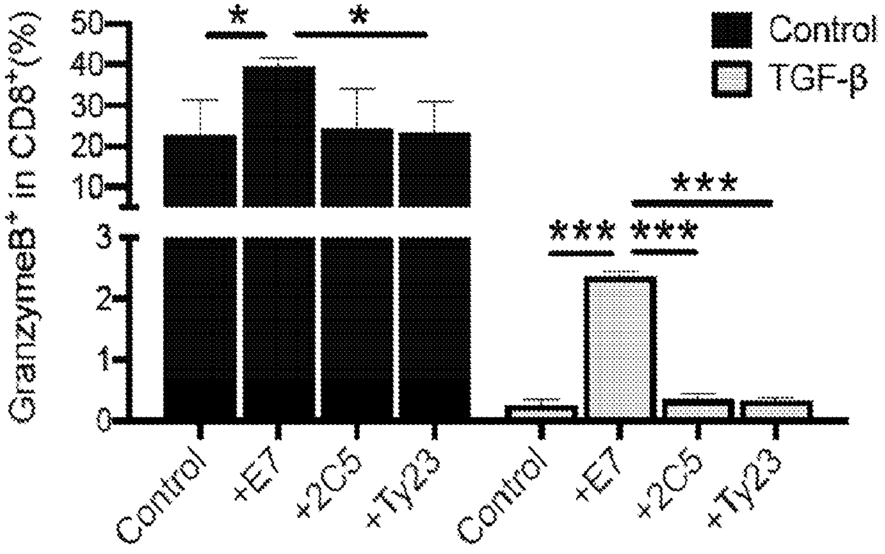
FIG. 2D

Effector
*Granzyme B, IFN-g, MIP-1a, TNF-a*

Stimulatory
*GM-CSF, IL-12p70, IL-18, IL-2, IL-21, IL-5, IL-7*

Chemoattractive
*BCA-1, CCL-11, IP-10, RANTES*

Regulatory
*FAS, IL-10, IL-13, IL-27, IL-4, sCD137*

Inflammatory
*IL-17A, IL-1b, IL-6, MCP-1*

Other
*KC, TGF-b*

FIG. 5

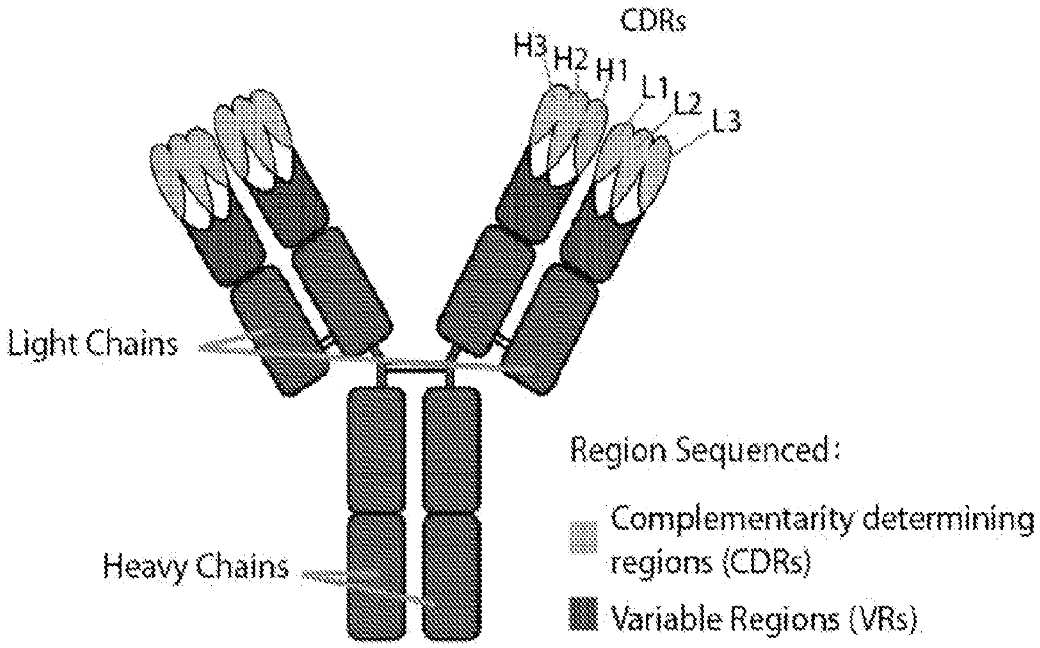

Heavy Chain DNA Sequence (SEQ ID NO: 3)
gaggtgcagctgcaggagtctggacctgagctggtgaatcctggggcctcagtgaagatttcctgcaaagcttctggctacgctttcaat
acgtactggataaactgggtgatgcagaggcctggaaagggtcttgaatggattggacggatttatcctggaggtggacatactaact
acaatgggaaattcaagggcaaggccatactgactgcagacagttcctccagtacagcctatatgcaactcagcagcctgacatctg
aggactctgcggtctacttctgtgcaagacccagtgatccctattactttgttatggactactggggtcaaggaacctcagtcaccgtctcc
gcag

Predicted Protein Sequence (SEQ ID NO: 4)
*Complementarity determining regions (CDRs) are underlined.*
EVQLQESGPELVNPGASVKISCKASGYAFNTYWINWVMQRPGKGLEWIGRIYPGGGHTNYNG
KFKGKAILTADSSSSTAYMQLSSLTSEDSAVYFCARPSDPYYFVMDYWGQGTSVTVSA

Light Chain DNA Sequence (SEQ ID NO: 1)
gatattgtgctgacgcaggctgcattctccagtccagtcactcttggaacgtcagcttccatctcctgcaggtctagtaagagtctcctgca
tagtgatggcttcacttatttgtattggtatctgcagaggccaggccagtctcctcagctcctgatatatcggatgtccaaccttgcctcagc
agtcccagacaggttcagtggcagtgggtcaggaactgatttcacactgagaatcagcagagtgggggctgaggatgtgggtgtttat
tactgtgctcaaatgctagaattcccgtacacgttcggaggggggaccaagctggaaatcaaac

Predicted Protein Sequence (SEQ ID NO: 2)
*Complementarity determining regions (CDRs) are underlined.*
DIVLTQAAFSSPVTLGTSASISCRSSKSLLHSDGFTYLYWYLQRPGQSPQLLIYRMSNLASAVP
DRFSGSGSGTDFTLRISRVGAEDVGVYYCAQMLEFPYTFGGGTKLEIK

ANTI-CD73 MONOCLONAL ANTIBODIES

CROSS-REFERENCE TO RELATED APPLICATIONS

This application is a U.S. National Phase Application under 35 U.S.C. § 371 of International Application No. PCT/US2022/017302, filed Feb. 22, 2022, which claims priority to U.S. Provisional Patent Application No. 63/152,116, filed Feb. 22, 2021, each of which are incorporated by reference in their entireties.

FIELD

Provided herein are monoclonal antibodies (mAbs) that bind to human Cluster of Differentiation 73 (CD73). In particular, anti-CD73 mAbs are provided that bind to and inhibit the activity of human CD73.

BACKGROUND

CD73, known as ecto-5'-nucleotidase, is an emerging immune checkpoint associated with adenosine metabolism that promotes tumor progression by inhibiting antitumor immune response and promoting angiogenesis. CD73 expression level is higher in the majority of human solid tumors. Its expression and activity are closely correlated with tumor invasiveness and metastasis. Thus, CD73 expression is often associated with worse prognosis and poor response to therapeutic agents. Besides the intrinsic tumor-promoting effect of CD73 by tumor cells, CD73 along with other adenosinergic molecules play key roles in fostering an immunosuppressive tumor microenvironment by affecting multiple types of immune cells including immune suppressor cells and immune effector cells. The inhibition of CD73 using monoclonal antibodies (mAb) or small molecular inhibitors, in combination with immune checkpoint blockade, targeted therapy or conventional therapy, improves antitumor effects in numerous preclinical mouse models of cancer. Several inhibitors targeting CD73 and/or adenosine receptor A2AR are currently being developed and tested in over 30 clinical trials. Accumulating data reveal that the combination of anti-CD73/A2AR and immune checkpoint blockade has promising clinical activity in patients with advanced solid tumors.

SUMMARY

Provided herein are monoclonal antibodies (mAbs) that bind to human Cluster of Differentiation 73 (CD73). In particular, anti-CD73 mAbs are provided that bind to and inhibit the activity of human CD73.

In some embodiments, provided herein are CD73 binding agents comprising a light chain variable region comprising complementarity determining regions CDR1, CDR2, and CDR3 having amino acid sequences of SEQ ID NOS: 5, 6, and 7, respectively; and a heavy chain variable region comprising complementarity determining regions CDR1, CDR2, and CDR3 having amino acid sequences of SEQ ID NOS: 8, 9, and 10, respectively. In some embodiments, the light chain variable region comprises 70% or greater (70%, 75%, 80%, 85%, 90%, 95%, 99%, 100%, or ranges therebetween) sequence identity with SEQ ID NO: 2. In some embodiments, the heavy chain variable region comprises 70% or greater (70%, 75%, 80%, 85%, 90%, 95%, 99%, 100%, or ranges therebetween) sequence identity with SEQ ID NO: 4.

In some embodiments, provided herein are immunoglobulin light chain polypeptides comprising 70% or greater (70%, 75%, 80%, 85%, 90%, 95%, 99%, 100%, or ranges therebetween) sequence identity with SEQ ID NO: 2. In some embodiments, provided herein are immunoglobulin light chain polypeptides comprising 90% or greater (e.g., 90%, 95%, 100%) sequence similarity with SEQ ID NO: 2. In some embodiments, an immunoglobulin light chain polypeptide herein comprises complementarity determining regions CDR1, CDR2, and CDR3 having amino acid sequences of SEQ ID NOS: 5, 6, and 7, respectively. In some embodiments, provided herein are CD73 binding agent comprising an immunoglobulin light chain polypeptide herein.

In some embodiments, provided herein are immunoglobulin heavy chain polypeptides comprising 70% or greater (70%, 75%, 80%, 85%, 90%, 95%, 99%, 100%, or ranges therebetween) sequence identity with SEQ ID NO: 4. In some embodiments, provided herein are immunoglobulin heavy chain polypeptides comprising 90% or greater (e.g., 90%, 95%, 100%) sequence similarity with SEQ ID NO: 4. In some embodiments, an immunoglobulin heavy chain polypeptide herein comprises complementarity determining regions CDR1, CDR2, and CDR3 having amino acid sequences of SEQ ID NOS: 8, 9, and 10, respectively. In some embodiments, provided herein are CD73 binding agent comprising an immunoglobulin heavy chain polypeptide herein.

In some embodiments, a CD73 binding agent herein is an antibody or antibody fragment. In some embodiments, a CD73 binding agent herein is selected from a Fab, F(ab')2, monospecific Fab2, monovalent antibody, scFv-Fc, and minibody. In some embodiments, a CD73 binding agent herein inhibits the activity of human CD73. In some embodiments, a CD73 binding agent herein mediates internalization of human CD73. In some embodiments, provided herein are compositions comprising a CD73 binding agent herein and a pharmaceutically acceptable carrier. In some embodiments, provided herein are nucleic acids encoding a CD73 binding agent herein. In some embodiments, provided herein are vectors or cells comprising a nucleic acid encoding a CD73 binding agent herein.

In some embodiments, provided herein are methods of treating a cancer or an infectious disease in a mammal, the methods comprising administering an effective amount of a composition comprising a CD73 binding agent herein, a nucleic acid encoding a CD73 binding agent herein, or a vector or cell comprising a CD73 binding agent herein to a mammal having a cancer or an infectious disease, whereupon the cancer or infectious disease is treated in the mammal. In some embodiments, the composition, nucleic acid, cell, or vector is administered to a mammal having a cancer. In some embodiments, the cancer is melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, ovarian cancer, pancreatic cancer, or Merkel cell carcinoma. In some embodiments, the mammal is a human. In some embodiments, methods further comprise co-administering one or more additional therapeutic agents. In some embodiments, the one or more additional therapeutic agents are selected from chemotherapeutics and immunotherapeutics. In some embodiments, provided herein is the use of a composition comprising a CD73 binding agent herein, a nucleic acid encoding a CD73 binding agent herein, or a vector or cell comprising a CD73 binding agent herein in the treatment or prevention of cancer or an infectious disease.

In some embodiments, provided herein is the use of a composition comprising a CD73 binding agent herein, a nucleic acid encoding a CD73 binding agent herein, or a vector or cell comprising a CD73 binding agent herein in the treatment or prevention of cancer or an infectious disease. In some embodiments, provided herein is the use of a composition comprising a CD73 binding agent herein, a nucleic acid encoding a CD73 binding agent herein, or a vector or cell comprising a CD73 binding agent herein for use as a medicament. In some embodiments, provided herein is the use of a composition comprising a CD73 binding agent herein, a nucleic acid encoding a CD73 binding agent herein, or a vector or cell comprising a CD73 binding agent herein for use in the manufacture of a medicament. In some embodiments, provided herein is use of a composition comprising a CD73 binding agent herein, a nucleic acid encoding a CD73 binding agent herein, or a vector or cell comprising a CD73 binding agent herein in the manufacture of a medicament for use in a method of treatment or prevention of cancer or an infectious disease.

BRIEF DESCRIPTION OF THE FIGURES

FIG. 1. E7 binds to CD73 and reduces the CD73 expression on murine CD8+ T cells. Splenocytes from C57BL/6 mice were cultured with or without commercial CD73 blockade anti-mCD73 Ab (TY23) in the presence of anti-CD3 and TGF-β. After 3 days, splenocytes were stained with E7 with secondary antibody. (A) MFI of E7 was measured by flow cytometry and summarized in (B). Splenocytes from C57BL/6 mice were cultured in the presence of anti-CD3. After 3 days, E7 was added into the culture for 20 mins and inducible CD73 expression on CD8+ T cells by TGF-β was measured by flow cytometry (C). Splenocytes from C57BL/6 mice were cultured with or without E7 for 5 days in the presence of anti-CD3. CD73 expression on CD8+ T cells was measured by flow cytometry (D). Data are represented as mean±SEM (*p<0.05)

FIG. 2. E7 overcomes TGF-β-mediated inhibitory effect on murine CD8+ T cell responses. Splenocytes from C57BL/6 mice were cultured with or without indicated antibodies including 2C5 from Astrazeneca and the commercial TY23 in the presence of anti-CD3 with or without TGF-β. After 5 days, IFN-γ (A, B) and granzyme B (C, D) by CD8+ T cells were measured by flow cytometry and summarized. Data are represented as mean±SEM (*p<0.05, ***p<0.001)

FIG. 5. Variable Region cDNA Sequence Analysis of E7. DNA sequence data analysis from the E7 hybridoma cell line culture were performed and consensus sequences for heavy and light chain were determined.

DEFINITIONS

Figure 3A:
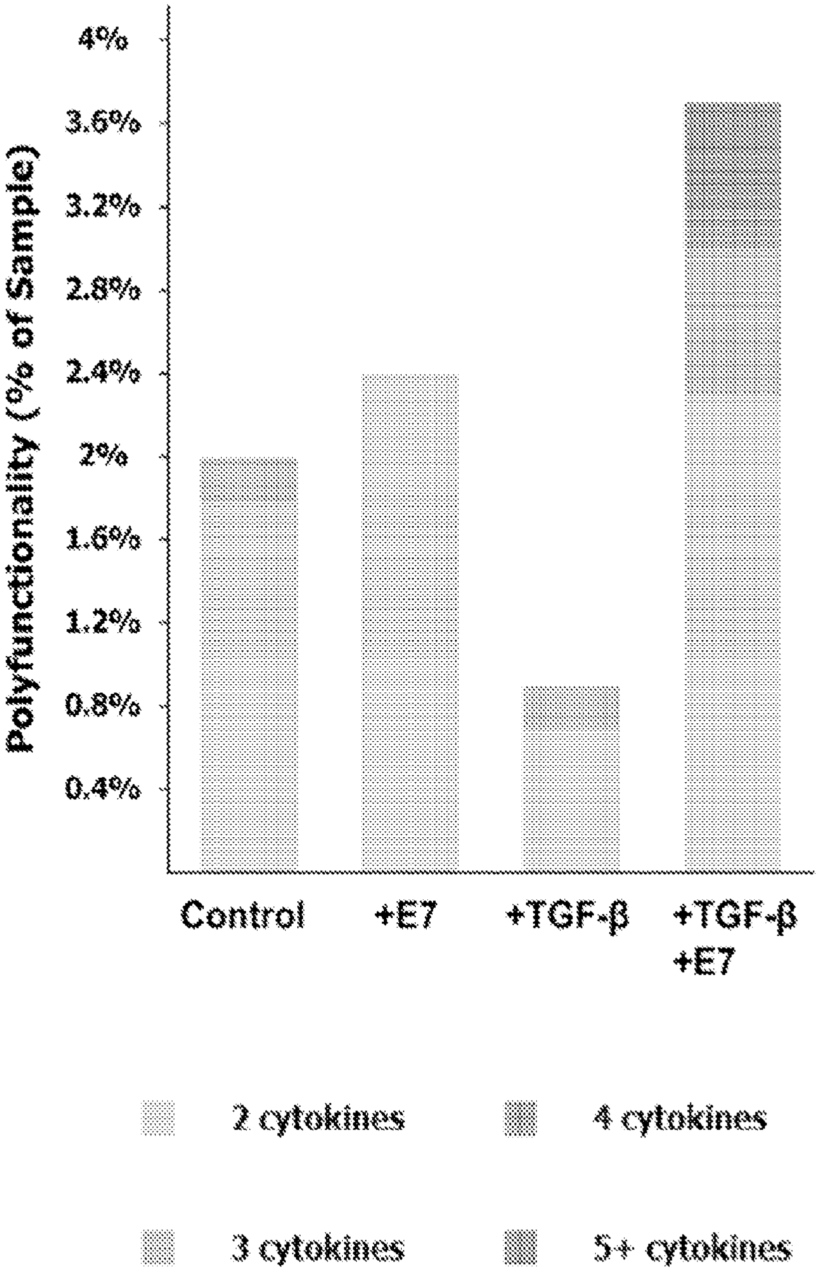
FIG. 3. E7 overcomes TGF-β-mediated inhibitory effect on human CAR T cell polyfunctionality. Human CAR-T were cultured with or without E7 or TGF-β in the presence of IL-2. After 3 days, multiplexed antibody coated chip was utilized that allows analyzing thousands of CAR T-cells at the single-cell level for the frequency and intensity of secretion of indicated cytokines (IsoCode Chip from Isoplexis). (A) Single cell polyfunctionality and (B) polyfunctional strength index graphs were analyzed and summarized by Isospeak.
Figure 3B:
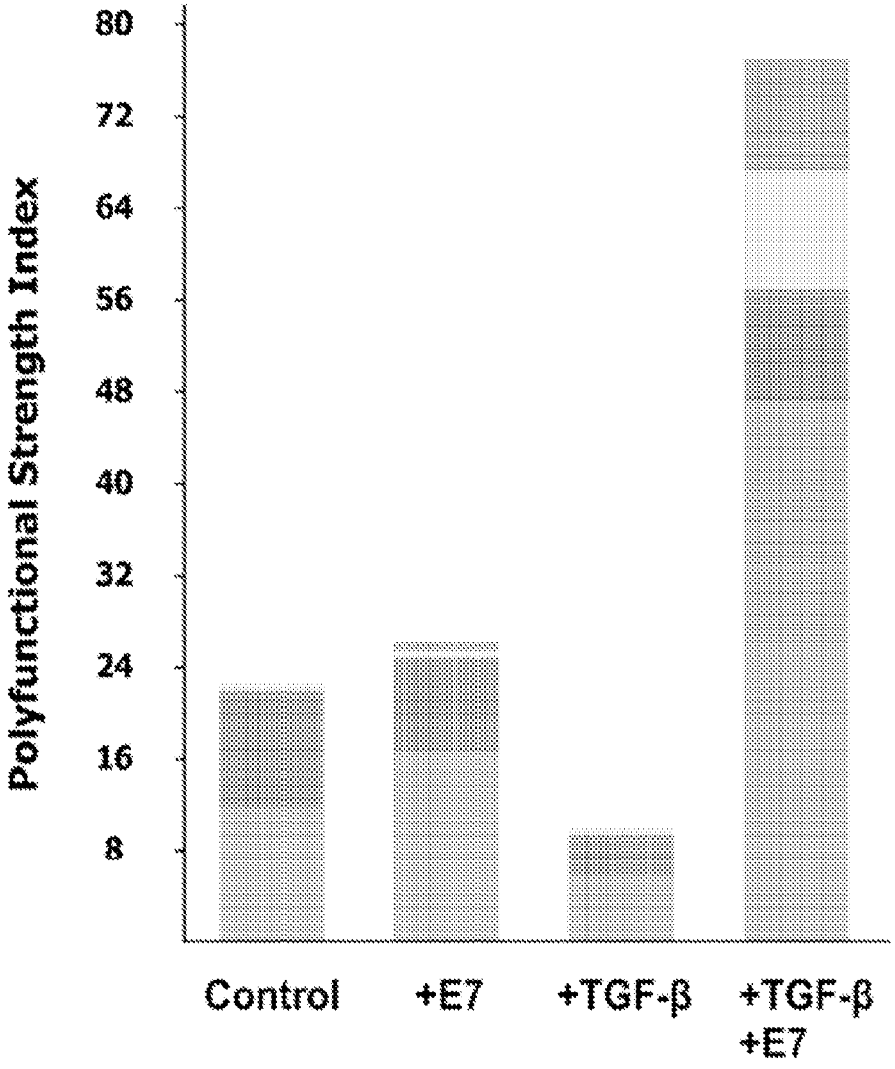
Figure 4:
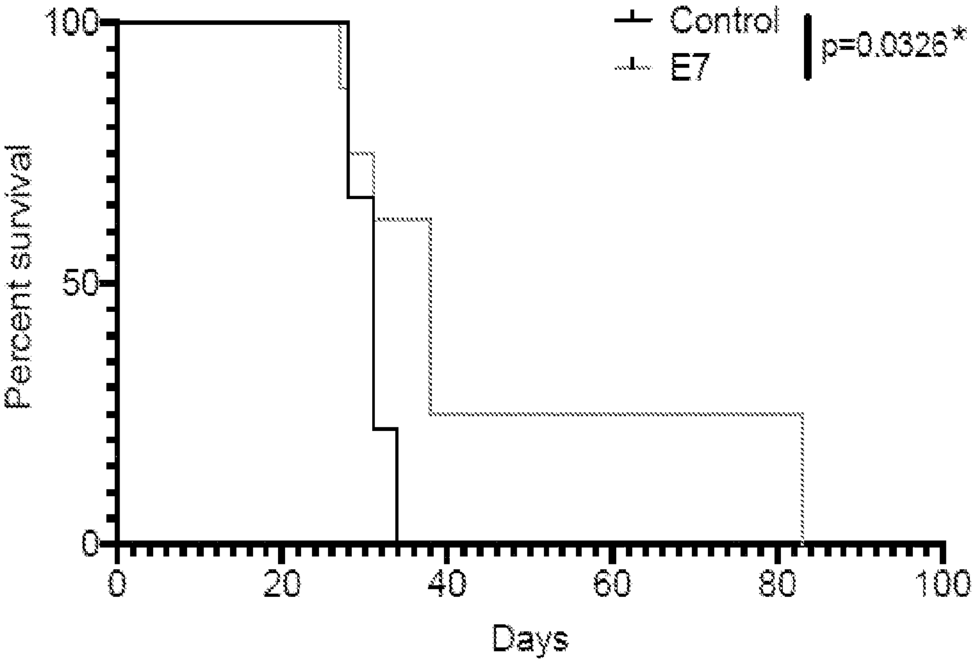
FIG. 4. E7 increases survival of ID8 ovarian tumor-bearing mice. ID8 ovarian tumor-bearing C57BL/6 mice were treated with control IgG or E7. (A) Survival curves for treated group and control group. Shown are 8 mice per group. Data are represented as mean±SEM (*p=0.0326)

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "antibody" refers to a whole antibody molecule or a fragment thereof (e.g., fragments such as Fab, Fab', and F(ab')2), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antiegen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', $F(ab')_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody). produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "$F(ab')_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made.

For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo. In some embodiments, by neutralizing the polypeptide comprising the epitope, the neutralizing antibody inhibits the capacity of the organism (or virus) displaying the epitope. For example, a "CD73 neutralizing antibody" reduces the activity of CD73.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "artificial" refers to compositions and systems that are designed or prepared by man, and are not naturally occurring. For example, an artificial polypeptide (e.g., antibody or antibody fragment) or nucleic acid is one comprising a non-natural sequence (e.g., a polypeptide without 100% identity with a naturally-occurring protein or a fragment thereof).

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("Octan"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "artificial polypeptide", "artificial antibody", or "artificial binding agent", consistent with the definition of "artificial" above, refers to a polypeptide, antibody, or binding agent having a distinct amino acid sequence or chemical makeup from those found in natural polypeptides, antibodies, and binding agents. An artificial polypeptide or antibody is not a subsequence of a naturally occurring protein, either the wild-type (i.e., most abundant) or mutant versions thereof. An "artificial polypeptide", "artificial antibody", or "artificial binding agent", as used herein, may be produced or synthesized by any suitable method (e.g., recombinant expression, chemical synthesis, enzymatic synthesis, purification from whole animal, etc.).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics (e.g., chemically modified peptides, peptoids (side chains are appended to the nitrogen atom of the peptide backbone, rather than to the α-carbons), β-peptides (amino group bonded to the β carbon rather than the α carbon), etc.) and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence.

The term "effective dose" or "effective amount" refers to an amount of an agent, e.g., a neutralizing antibody, that results in the reduction of symptoms in a patient, treatment of prevention of a disease or condition, or results in a desired biological outcome.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition (e.g., a cancer) as well as individuals who are at risk of acquiring a particular condition or disorder. The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term pharmaceutical composition" refers to the combination of an active agent (e.g., binding agent) with a carrier, inert or active, making the composition especially suitable for diagnostic or therapeutic use in vitro, in vivo or ex vivo.

The terms “pharmaceutically acceptable” or “pharmacologically acceptable,” as used herein, refer to compositions that do not substantially produce adverse reactions, e.g., toxic, allergic, or immunological reactions, when administered to a subject.

As used herein, the term “pharmaceutically acceptable carrier” refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington’s Pharmaceutical Sciences, 15th Ed., Mack Publ. Co., Easton, Pa. (1975), incorporated herein by reference in its entirety.

DETAILED DESCRIPTION

Provided herein are monoclonal antibodies (mAbs) that bind to human Cluster of Differentiation 73 (CD73). In particular, anti-CD73 mAbs are provided that bind to and inhibit the activity of human CD73.

Experiments were conducted during development of embodiments herein to generate an anti-CD73 mAb (“E7”, mouse IgG2b) by hybridoma technology, which binds to both human and murine CD73. Data from experiments conducted during development of embodiments herein demonstrate that the E7 overcomes TGF-β-mediated inhibitory effect on murine CD8+ T cell responses and human CAR T cell polyfunctionality in vitro, which is superior to other available anti-CD73 mAbs. E7 treatment provides enhanced survival of ovarian tumor-bearing mice, indicating its therapeutic utility in cancer therapy.

The invention provides an isolated immunoglobulin heavy chain polypeptide and/or an isolated immunoglobulin light chain polypeptide, or a fragment (e.g., antigen-binding fragment) thereof. Immunoglobulins or antibodies are a proteins found in blood or other bodily fluids of vertebrates, which are used by the immune system to identify and neutralize foreign objects, such as bacteria and viruses. Such a polypeptide is isolated when it is removed from its natural environment. In certain embodiments, an immunoglobulin or antibody is a protein that comprises at least one complementarity determining region (CDR). The CDRs form the hypervariable region of an antibody, which is responsible for antigen binding. A whole immunoglobulin typically consists of four polypeptides: two identical copies of a heavy (H) chain polypeptide and two identical copies of a light (L) chain polypeptide. Each of the heavy chains contains one N-terminal variable (VH) region and three C-terminal constant (CHI, CH2, and CH3) regions, and each light chain contains one N-terminal variable (VL) region and one C-terminal constant (CL) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The VH and VL regions have the same general structure, with each region comprising four framework (FW or FR) regions. The framework region refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), Immunobiology, 5th Ed., Garland Publishing, New York, NY (2001); incorporated by reference in its entirety).

The framework regions are connected by three complementarity determining regions (CDRs). As discussed above, the three CDRs, known as CDR1, CDR2, and CDR3, form the hypervariable region of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The isolated immunoglobulin heavy chain polypeptide and the isolated immunoglobulin light chain polypeptide of the invention desirably bind to CD73. As discussed throughout, Cluster of Differentiation 73 (CD73), also known as ecto-5'-nucleotidase (ecto-5'NT, EC 3.1.3.5), is a glycosylphosphatidylinositol (GPI)-linked cell surface enzyme found in most tissues, but particularly expressed in endothelial cells and subsets of hematopoietic cells (Resta et al., Immunol Rev 1998; 161:95-109 and Colgan et al., Prinergic Signal 2006; 2:351-60; incorporated by reference in their entireties). CD73 catalyzes the dephosphorylation of extracellular nucleoside monophosphates into nucleosides, such as adenosine. Adenosine is a widely studied signaling molecule which mediates its biological effects through several receptors, including A1, A2A, A2B, and A3. Adenosine has been shown to regulate proliferation and migration of many cancers and to have an immunosuppressive effect through the regulation of anti-tumor T cells (Zhang et al., Cancer Res 2010; 70:6407-11; incorporated by reference in its entirety).

CD73 has been reported to be expressed on many different cancers, including colon, lung, pancreas, ovary, bladder, leukemia, glioma, glioblastoma, melanoma, thyroid, esophageal, prostate and breast cancers (Jin et al., Cancer Res 2010; 70:2245-55 and Stagg et al., PNAS 2010; 107: 1547-52; incorporated by reference in its entirety). Moreover, CD73 expression in cancer has been linked to increased proliferation, migration, neovascularization, invasiveness, metastasis and shorter patient survival. CD73 activity has also been proposed as a prognostic marker in papillary thyroid carcinomas. While CD73 has been shown to regulate cell-cell and cell-matrix interactions on tumor cells, CD73 expression and activity has also been linked to reduced T-cell responses and implicated in drug resistance (Spychala et al., Pharmacol Ther 3000; 87:161-73; incorporated by reference in its entirety). Thus, CD73 regulates cancer progression both directly and indirectly.

In some embodiments, provided herein is an isolated immunoglobulin heavy chain polypeptide and an isolated immunoglobulin light chain polypeptide that bind to CD73. In some embodiments, provided herein are CD73 binding agents (e.g., antibodies, antibody fragments, etc.) that comprise the aforementioned immunoglobulin heavy chain polypeptide, immunoglobulin light chain polypeptide, and/or the complementarity-determining regions (CDRs) thereof.

In certain embodiments, the anti-CD73 binding agents (e.g., antibodies, antibody fragments, etc.) exhibit at least one of the following properties: binding to human, mouse, and/or other mammalian CD73; inhibition of CD73 enzymatic activity (e.g., human CD73, mouse CD73, and/or other mammalian CD73); antibody-mediated internalization of CD73 into cells, e.g., tumor cells; and binding to a conformational epitope of CD73.

In certain embodiments, the anti-CD73 binding agents (e.g., antibodies, antibody fragments, etc.) or antigen binding portions thereof, bind to an epitope on human CD73 (SEQ ID NO: 11). In some embodiments, the anti-CD73 binding agents (e.g., antibodies, antibody fragments, etc.) or antigen binding portions thereof, bind to an epitope on mouse CD73 (SEQ ID NO: 12) or other mammalian CD73 or homologs thereof.

In some embodiments, a polypeptide is provided comprising three CDRs of SEQ ID NOS: 5, 6, and 7. In some embodiments, a polypeptide is provided comprising 70% or greater (e.g., 70%, 75%, 80%, 85%, 90%, 95%, 100%) sequence similarity with SEQ ID NO: 2. In some embodiments, a polypeptide is provided comprising 70% or greater (e.g., 70%, 75%, 80%, 85%, 90%, 95%, 100%) sequence identity with SEQ ID NO: 2. In some embodiments, a polypeptide comprises a degree (e.g., 70%, 75%, 80%, 85%, 90%, 95%, 100%) of sequence similarity and/or identity with SEQ ID NO: 2 and comprises CDRs of SEQ ID NOS: 5, 6, and 7. In some embodiments, a polypeptide comprises a light chain variable region or a CD73 binding agent (e.g., antibody, antibody fragment, etc.).

In some embodiments, a polypeptide is provided comprising three CDRs of SEQ ID NOS: 8, 9, and 10. In some embodiments, a polypeptide is provided comprising 70% or greater (e.g., 70%, 75%, 80%, 85%, 90%, 95%, 100%) sequence similarity with SEQ ID NO: 4. In some embodiments, a polypeptide is provided comprising 70% or greater (e.g., 70%, 75%, 80%, 85%, 90%, 95%, 100%) sequence identity with SEQ ID NO: 4. In some embodiments, a polypeptide comprises a degree (e.g., 70%, 75%, 80%, 85%, 90%, 95%, 100%) of sequence similarity and/or identity with SEQ ID NO: 4 and comprises CDRs of SEQ ID NOS: 8, 9, and 10. In some embodiments, a polypeptide comprises a heavy chain variable region or a CD73 binding agent (e.g., antibody, antibody fragment, etc.).

In some embodiments, a CD73 binding agent (e.g., antibody, antibody fragment, etc.) comprises three variable heavy chain CDRs (e.g., CDRs of SEQ ID NOS: 8, 9, and 10) and the three variable light chain CDRs (e.g., CDRs of SEQ ID NOS: 5, 6, and 7) that are in the variable heavy chain and variable light chain pairs of anti-CD73 antibodies described herein.

In some embodiments, provided herein is an immunoglobulin heavy chain polypeptide that comprises a CDR amino acid sequence of SEQ ID NO: 8, a CDR amino acid sequence of SEQ ID NO: 9, and a CDR3 amino acid sequence of SEQ ID NO: 10. In some embodiment, the isolated immunoglobulin heavy chain polypeptide comprises, consists of, or consists essentially of a CDR amino acid sequence of SEQ ID NO: 8, a CDR amino acid sequence of SEQ ID NO: 9, and a CDR3 amino acid sequence of SEQ ID NO: 10.

In some embodiments, provided herein is an immunoglobulin light chain polypeptide that comprises a CDR amino acid sequence of SEQ ID NO: 5, a CDR amino acid sequence of SEQ ID NO: 6, and a CDR3 amino acid sequence of SEQ ID NO: 7. In some embodiment, the isolated immunoglobulin light chain polypeptide comprises, consists of, or consists essentially of a CDR amino acid sequence of SEQ ID NO: 5, a CDR amino acid sequence of SEQ ID NO: 6, and a CDR3 amino acid sequence of SEQ ID NO: 7.

In some embodiments, provided herein is an immunoglobulin heavy chain polypeptide that comprises an amino acid sequence of SEQ ID NO: 4. In some embodiments, the isolated immunoglobulin heavy chain polypeptide comprises, consists of, or consists essentially of an amino acid sequence of SEQ ID NO: 4.

In some embodiments, provided herein is an immunoglobulin light chain polypeptide that comprises an amino acid sequence of SEQ ID NO: 2. In some embodiments, the isolated immunoglobulin light chain polypeptide comprises, consists of, or consists essentially of an amino acid sequence of SEQ ID NO: 2.

In some embodiments, provided herein are CDR sequences comprising substitutions relative to the CDRs provided herein (e.g., SEQ ID NOS: 5-10). In some embodiments, CDRs, combinations thereof, and polypeptides comprising such CDRs (e.g., immunoglobulin light/heavy chain polypeptides) are provide comprising 1, 2, 3, 4, 5, 6, or more substitutions relative to SEQ ID NOS: 5-10. In some embodiments, substitutions are conservative or semi-conservative substitutions. In some embodiments, polypeptides comprising combinations of such CDRs bind the same CD73 epitope(s) as the binding agents comprising CDRs of SEQ ID NOS: 5-10.

In some embodiments, provided herein are immunoglobulin heavy chain polypeptides and/or immunoglobulin light chain polypeptides having substitutions relative to SEQ ID NO: 4 and 2. In some embodiments, substitutions are conservative or semi-conservative substitutions. In some embodiments, polypeptides are provided comprising substitutions relative to SEQ ID NO: 4 and 2 that bind the same CD73 epitope(s) as the binding agents comprising SEQ ID NO: 4 and 2. In some embodiments, substitutions to SEQ ID NO: 4 and/or 2 are made to portions of the polypeptide other than those corresponding to SEQ ID NOS: 8-10 and/or 5-7. In some embodiments, provided herein are polypeptides comprising 70% or greater (e.g., 70%, 75%, 80%, 85%, 90%, 95%, 99%, or more or ranges therebetween (e.g., 90% or more)) sequence identity or sequence similarity to SEQ ID NO: 4 or 2 and having 100% sequence similarity and/or identity with each of SEQ ID NOS: 8-10 or 5-7.

In some embodiments, one or more amino acids are inserted into the immunoglobulin heavy or light chain polypeptides described herein. Any number of any suitable amino acids can be inserted into the amino acid sequence of the immunoglobulin heavy/light chain polypeptides. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy/light chain polypeptide. In some embodiments, 1-10 amino acids (e.g., 1, 2, 3, 4, 5, 6, 7, 8, 9, or 10 amino acids) are inserted into the amino acid sequence of the immunoglobulin heavy/light chain polypeptides. In some embodiments, the amino acid(s) are inserted into an immunoglobulin heavy/light chain polypeptide described herein in any suitable location. In some embodiments, the amino acid(s) are inserted into a CDR of the immunoglobulin heavy/light chain polypeptides. In certain embodiments, the amino acid(s) are inserted into a region other than the CDRs of the immunoglobulin heavy/light chain polypeptides.

In some embodiments, provided herein are CD73-binding agents comprising, consisting essentially of, or consisting of the amino acid sequences described herein. Preferably, the CD73-binding agent is an antibody or a fragment (e.g., immunogenic fragment) thereof. The isolated CD73-binding agent of the invention comprises, consists essentially of, or consists of the inventive isolated immunoglobulin heavy chain polypeptide and/or the inventive isolated immunoglobulin light chain polypeptide. In one embodiment, the CD73-binding agent comprises, consists essentially of, or consists of the immunoglobulin heavy chain polypeptide or the inventive immunoglobulin light chain polypeptide. In another embodiment, an isolated CD73-binding agent comprises, consists essentially of, or consists of the immunoglobulin heavy chain polypeptide and the inventive immunoglobulin light chain polypeptide.

The invention is not limited to an isolated CD73-binding agent that comprises, consists essentially of, or consists of an immunoglobulin heavy chain polypeptide and/or light chain polypeptide having replacements, insertions, and/or deletions of the specific amino acid residues disclosed herein. Indeed, any amino acid residue of the immunoglobulin heavy chain polypeptides and/or the immunoglobulin light chain polypeptides can be replaced, in any combination, with a different amino acid residue, or can be deleted or inserted, so long as a biological activity of the CD73-binding agent is maintained, enhanced, or improved as a result of the amino acid replacements, insertions, and/or deletions. The biological activity of a CD73-binding agent refers to, for example, binding affinity for CD73 or a particular CD73epitope, neutralization or inhibition of CD73 activity (e.g., $IC_{50}$), pharmacokinetics, and cross-reactivity (e.g., with non-human homo logs or orthologs of the CD73 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

A CD73-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al, Nat. Biotech., 23(9): 1126-1129 (2005); incorporated by reference in its entirety). An isolated CD73 binding agent may contain any CD73-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and CHi domains, (ii) a $F(ab')_2$ fragment, which is a bivalent fragment comprising two Fab fragments linked by a disulfide bridge at the hinge region, (iii) a Fv fragment consisting of the $V_L$ and VII domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a domain antibody (dAb), which is an antibody single variable region domain ($V_H$ or $V_L$) polypeptide that specifically binds antigen.

In embodiments where the isolated CD73-binding agent comprises a fragment of the immunoglobulin heavy chain or light chain polypeptide, the fragment can be of any size so long as the fragment binds to, and preferably inhibits the activity of, a CD73 protein. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the CD73-binding agent is an antibody or antibody fragment, the antibody or antibody fragment desirably comprises a heavy chain constant region (Fe) of any suitable class. Preferably, the antibody or antibody fragment comprises a heavy chain constant region that is based upon wild-type IgG1, IgG2, or IgG4 antibodies, or variants thereof.

The CD73-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al, Science, 242: 421-426 (1988); Huston et al, Proc. Natl. Acad. Sci. USA, 85: 5879-5883 (1988); and Osbourn et al, Nat. Biotechnol, 16: 778 (1998); incorporated by reference in their entireties) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024; incorporated by reference in its entirety.

A CD73-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include subcellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated CD73-binding agent also can be an antibody conjugate. In this respect, the isolated CD73-binding agent can be a conjugate of (1) an antibody, an alternative scaffold, or fragments thereof, and (2) a protein or non-protein moiety comprising the CD73-binding agent. For example, the CD73-binding agent can be all or part of an antibody conjugated to a peptide, a fluorescent molecule, or a chemotherapeutic agent.

The CD73-binding agent can be, or can be obtained from, a human antibody, a non-human antibody, or a chimeric antibody. By "chimeric" is meant an antibody or fragment thereof comprising both human and non-human regions. Preferably, an isolated CD73-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Kohler and Milstein, Eur. J. Immunol., 5: 511-519 (1976); Harlow and Lane (eds.), Antibodies: A Laboratory Manual, CSH Press (1988); and Janeway et al. (eds.), Immunobiology, 5th Ed., Garland Publishing, New York, NY (2001); incorporated by reference in their entireties. In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™ and the Kyowa Kirin KM-MOUSE™ (see, e.g., Lonberg, Nat. Biotechnol, 23(9): 1117-25 (2005), and Lonberg, Handb. Exp. Pharmacol, 181: 69-97 (2008); incorporated by reference in their entireties. A humanized antibody can be generated using any suitable method known in the art (see, e.g., An, Z. (ed.), Therapeutic Monoclonal Antibodies: From Bench to Clinic, John Wiley & Sons, Inc., Hoboken, New Jersey (2009); incorporated by reference in its entirety), including, e.g., grafting of non-human CDRs onto a human antibody scaffold (see, e.g., Kashmiri et al, Methods, 36(1): 25-34 (2005); and Hou et al, J. Biochem., 144(1): 115-120 (2008); incorporated by reference in their entireties). In one embodiment, a humanized antibody can be produced using the methods described in, e.g., U.S. Patent Application Publication 2011/0287485; incorporated by reference in its entirety.

The invention also provides one or more isolated or purified nucleic acid sequences that encode the inventive immunoglobulin heavy chain polypeptide (e.g., SEQ ID NO: 3), the inventive immunoglobulin light chain polypeptide (e.g., SEQ ID NO: 1) and any other amino acid sequences or CD73 binding agents described herein. The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

In some embodiments, provided herein are vectors comprising one or more nucleic acid sequences encoding the immunoglobulin heavy chain polypeptide, the immunoglobulin light chain polypeptide, and/or the CD73-binding agents described herein. The vector can be, for example, a plasmid, episome, cosmid, viral vector (e.g., retroviral or adenoviral), or phage. Suitable vectors and methods of vector preparation are well known in the art (see, e.g., Sambrook et al., Molecular Cloning, a Laboratory Manual, 3rd edition, Cold Spring Harbor Press, Cold Spring Harbor, N.Y. (2001), and Ausubel et al, Current Protocols in Molecular Biology, Greene Publishing Associates and John Wiley & Sons, New York, N.Y. (1994); incorporated by reference in their entireties).

In addition to nucleic acid sequences encoding the immunoglobulin heavy polypeptide, the immunoglobulin light chain polypeptide, and/or the CD73-binding agent, vectors in some embodiments comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, Gene Expression Technology: Methods in Enzymology, Vol. 185, Academic Press, San Diego, Calif. (1990); incorporated by reference in its entirety.

Vector(s) comprising the nucleic acid(s) encoding the inventive amino acid sequences herein can be introduced into a host cell that is capable of expressing the polypeptides encoded thereby, including any suitable prokaryotic or eukaryotic cell. As such, the invention provides an isolated cell comprising the inventive vector. Preferred host cells are those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102). Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia*, Rhino-sporidium, *Saccharomyces*, and *Schizosaccharomyces*. Preferred yeast cells include, for example, *Saccharomyces* cerivisae and *Pichia pastoris*. Exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art. In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al, Proc. Natl. Acad. Sci. USA, 85: 1581-1585 (1988)), Raji cells (CCL-86), and derivatives thereof.

A nucleic acid sequence encoding an amino acid sequence herein (or cd73 binding agent comprising such amino acid sequences) may be introduced into a cell by transfection, transformation, or transduction. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991); incorporated by reference in its entirety); DEAE-dextran; electroporation; cationic liposome-mediated transfection; tungsten particle-facilitated microparticle bombardment (Johnston, Nature, 346: 776-777 (1990); incorporated by reference in its entirety); and strontium phosphate DNA co-precipitation (Brash et al, Mol. Cell Biol, 7: 2031-2034 (1987); incorporated by reference in its entirety). Phage or viral vectors can be introduced into host cells, after growth of infectious particles in suitable packaging cells, many of which are commercially available. The invention provides a composition comprising an effective amount of the immunoglobulin heavy chain polypeptides herein, the immunoglobulin light chain polypeptides herein, a CD73-binding agent herein, nucleic acid sequence encoding any of the foregoing, or the vectors comprising such nucleic acid sequences. In some embodiments, a composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, PA (2001); incorporated by reference in its entirety.

Provided herein are methods of treating any disease or disorder in which the improper expression (e.g., overexpression) or increased activity of a CD73 protein causes or contributes to the pathological effects of the disease, or a decrease in CD73 protein levels or activity has a therapeutic benefit in mammals, preferably humans. The invention also provides a method of treating a cancer or an infectious disease in a mammal. The method comprises administering the aforementioned composition to a mammal having a cancer or an infectious disease, whereupon the cancer or infectious disease is treated in the mammal. As discussed herein, CD73 is abnormally expressed in a variety of cancers. The inventive method can be used to treat any type of cancer known in the art, such as, for example, melanoma, renal cell carcinoma, lung cancer, bladder cancer, ovarian cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. The inventive method can be used to treat any type of infectious disease (i.e., a disease or disorder caused by a bacterium, a virus, a fungus, or a parasite). Administration of a composition comprising a CCD73-binding agent, component thereof, nucleic acid sequence encoding any of the foregoing, or the vector comprising the such a nucleic acid sequence induces an immune response against a cancer or infectious disease in a mammal. An immune response can entail, for example, antibody production and/or the activation of immune effector cells (e.g., T-cells).

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the CD73-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the CD73-binding agent to elicit a desired response in the individual. For example, a therapeutically effective amount of a CD73-binding agent is an amount which decreases CD73 protein bioactivity in a human and/or enhances the immune response against a cancer or infectious disease.

Alternatively, the pharmacologic and/or physiologic effect may be prophylactic, i.e., the effect completely or partially prevents a disease or symptom thereof. In this respect, the inventive method comprises administering a "prophylactically effective amount" of the CD73-binding agent. A "prophylactically effective amount" refers to an amount effective, at dosages and for periods of time necessary, to achieve a desired prophylactic result (e.g., prevention of disease onset). Prevention of disease onset may not require 100% likelihood of disease onset being prevented. Rather, a disease is prevented in an individual if, when considered on a population basis, the likelihood of disease onset is reduced.

A typical dose can be, for example, in the range of 1 μg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1μ§/1¾ to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition herein can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive CD73-binding agent can be measured by any suitable method known in the art. For example, the biological activity can be assessed by determining the stability of a particular CD73-binding agent. In one embodiment of the invention, the CD73-binding agent (e.g., an antibody, antibody fragment) has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values).

The biological activity of a particular CD73-binding agent also can be assessed by determining its binding affinity to a CD73 protein or an epitope thereof. The term "affinity" refers to the equilibrium constant for the reversible binding of two agents and is expressed as the dissociation constant (KD). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In one embodiment, the CD73-binding agent can bind to a CD73 protein with a KD less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the CD73-binding agent can bind to CD73 with a KD less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, e.g., Janeway et al. (eds.), Immunobiology, 5th ed., Garland Publishing, New York, NY, 2001).

The CD73-binding agent of the invention may be administered alone or in combination with other drugs (e.g., as an adjuvant). For example, the CD73-binding agent can be administered in combination with other agents for the treatment or prevention of the diseases disclosed herein. In this respect, the CD73-binding agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. When the inventive method treats an infectious disease, the CD73-binding agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In another embodiment, the inventive CD73-binding agent can be administered in combination with other agents that inhibit immune checkpoint pathways. For example, the inventive CD73-binding agent can be administered in combination with agents that inhibit or antagonize the PD-1, CTLA-4, TIM-3 or LAG-3 pathways. Combination treatments that simultaneously target two or more immune checkpoint pathways have demonstrated improved and potentially synergistic antitumor activity (see, e.g., Sakuishi et al, J. Exp. Med., 207: 2187-2194 (2010); Ngiow et al, Cancer Res., 71: 3540-3551 (2011); and Woo et al., Cancer Res., 72: 917-927 (2012); incorporated by reference in their entireties).

In addition to therapeutic uses, the CD73-binding agent described herein can be used in diagnostic or research applications. In this respect, the CD73-binding agent can be used in a method to diagnose a cancer or infectious disease. In a similar manner, the CD73-binding agent can be used in an assay to monitor CD73-binding levels in a subject being tested for a disease or disorder that is associated with abnormal CD73 expression or activity. Research applications include, for example, methods that utilize the CD73-binding agent and a label to detect a CD73 protein in a sample, e.g., in a human body fluid or in a cell or tissue extract. The CD73-binding agent can be used with or without modification, such as covalent or non-covalent labeling with a detectable moiety. For example, the detectable moiety can be a radioisotope, a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al, Nature, 194: 495-496 (1962); David et al, Biochemistry, 13: 1014-1021 (1974); Pain et al, J. Immunol. Meth., 40: 219-230 (1981); and Nygren, J. Histochem. and Cytochem., 30: 407-412 (1982); incorporated by reference in their entireties).

CD73 protein levels can be measured using a CD73-binding agent by any suitable method known in the art. Such methods include, for example, radioimmunoassay (RIA), and FACS. Normal or standard expression values of CD73 protein can be established using any suitable technique, e.g., by combining a sample comprising, or suspected of comprising, a CD73 polypeptide with a CD73-binding agent under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, Monoclonal Antibodies: A Manual of Techniques, CRC Press, Inc. (1987)). In some embodiments, the amount of CD73 polypeptide expressed in a sample is then compared with a standard value.

The CD73-binding agent can be provided in a kit, i.e., a packaged combination of reagents in predetermined amounts with instructions for performing a diagnostic assay. If the CD73-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

EXPERIMENTAL

Figure 6A:
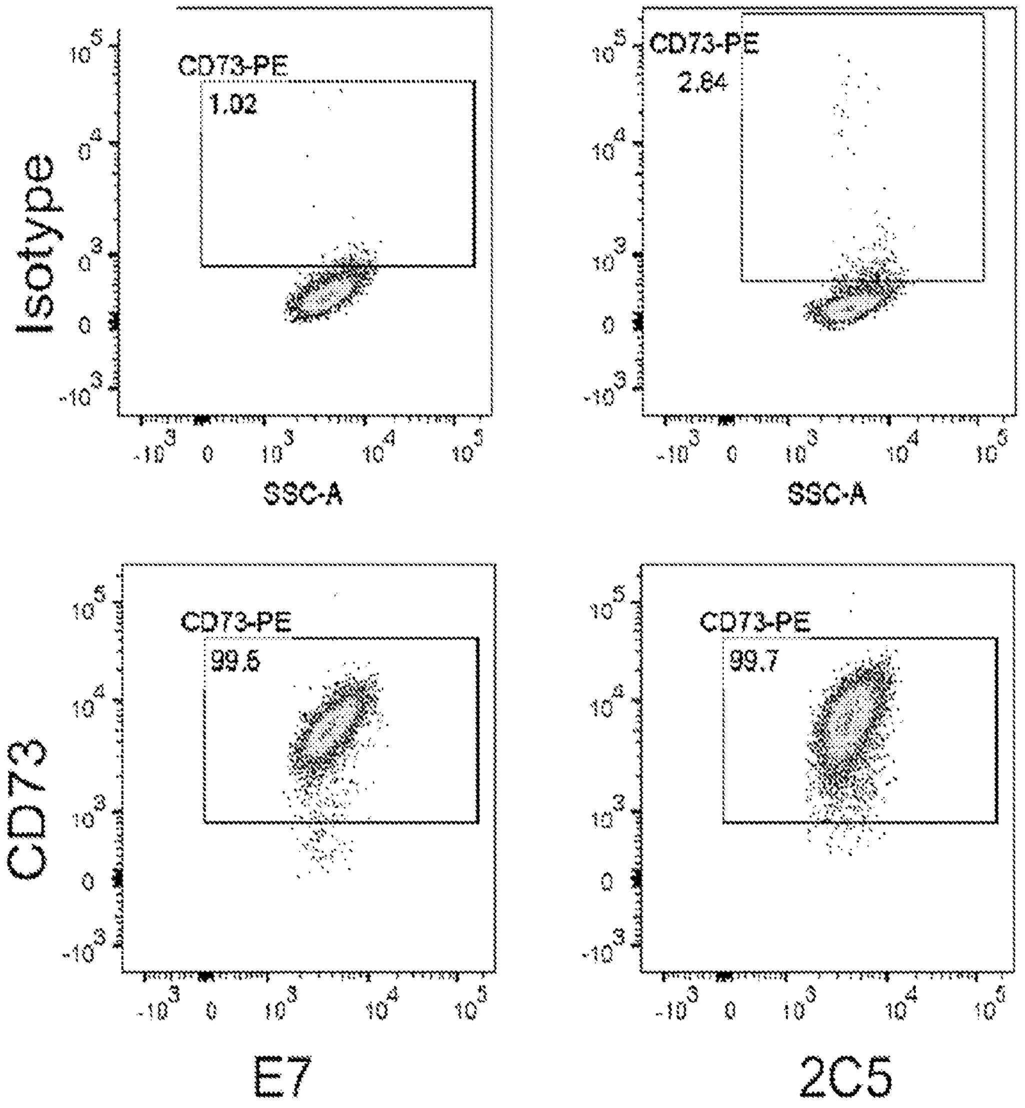
FIG. 6. E7 binds to CD73 on both human and mouse tumor cells. (A) Human prostate cancer cells PC3 were stained with E7 or 2C5 from Astrazeneca with secondary antibody. (B) Murine breast cancer cells E0771 and CD73 KO counterparts (knocked out by the CRISPR/Cas9 system) were stained with E7 with secondary antibody. CD73 expression on these tumor cells was measured by flow cytometry.
Figure 6B:
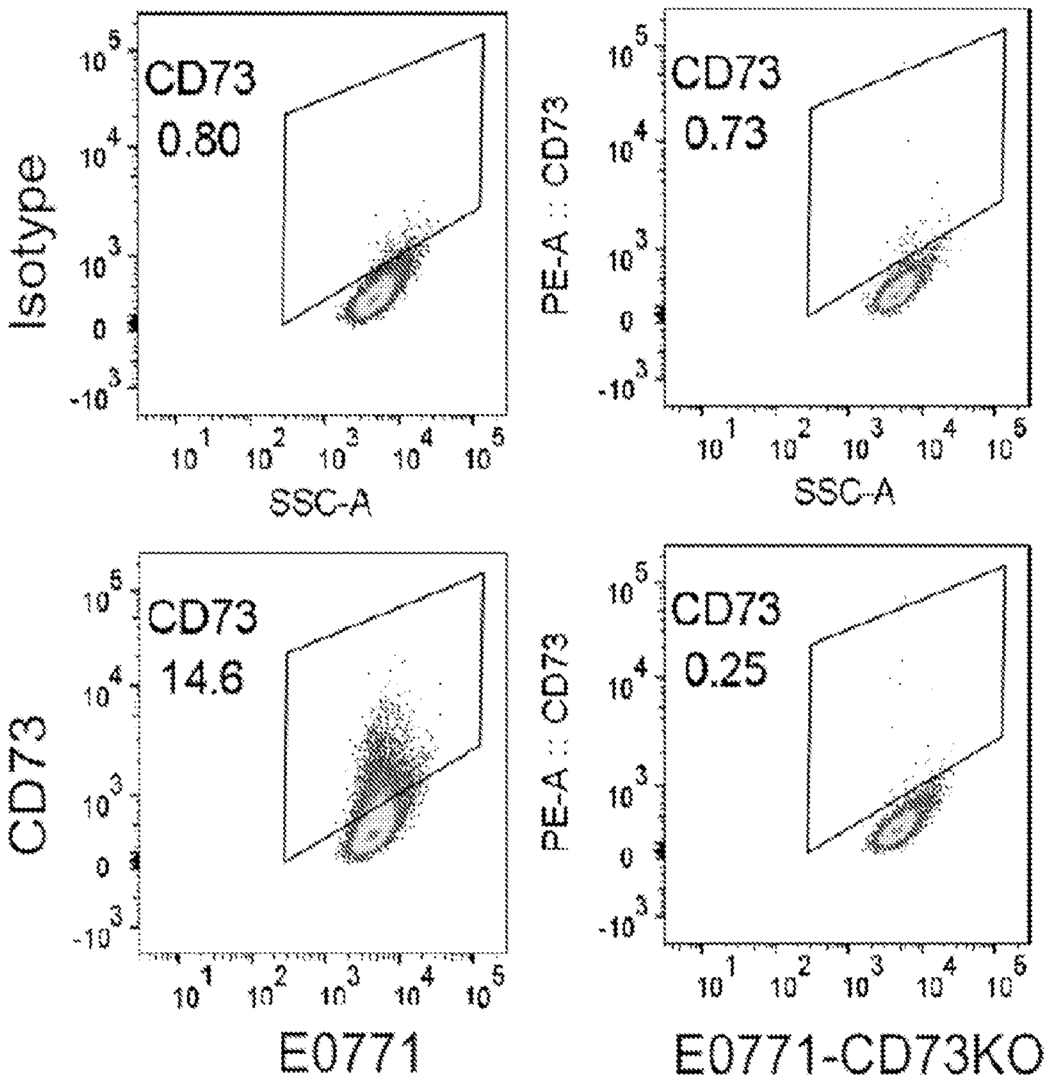

Experiments were conducted during development of embodiments herein to confirm the binding capacity of the anti-CD73 mAb (E7, mouse IgG2b) to CD73. Human prostate tumor cells (PC3) were stained with E7 or 2C5 (a commercially-available anti-CD73 mAb, Astrazeneca) at 10 μg/ml for 15 min followed by PE anti-mIgG secondary Ab for another 15 min. The isotype Ab (nonspecific mouse IgG2b) was used as control for staining in parallel. CD73 expression levels on these tumor cells were measured by flow cytometry. E7 was very effective to bind to CD73 on PC3 cells similar to 2C5 (FIG. 6A). Furthermore, the binding of E7 to CD73 was observed on murine breast cancer cells (E0771) (FIG. 6B left). These results indicated that E7 is able to efficiently bind to CD73 on both human and mouse tumor cells. The binding of E7 to CD73 was not detected on E0771 cells after CD73 knockout by the CRISPR-Cas9 system knockout (FIG. 16B right), confirming the specificity of E7-mediated cellular binding of CD73.

Figure 7A:
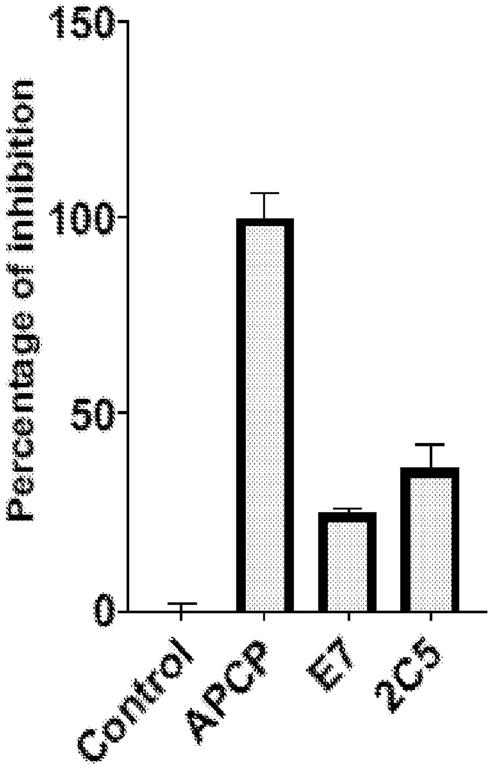
FIG. 7. E7 is capable of inhibiting the enzymatic activity of CD73 on both human and mouse tumor cells. CD73 enzymatic activity is determined by the luminescence-based CD73 Inhibitor screening assay (measuring degradation of extracellular AMP into adenosine). The small molecule inhibitor APCP was used as a positive control for normalization. Comparison of ability to inhibit CD73 activity between E7 and 2C5 anti-CD73 antibodies in both human PC3 prostate tumor cells (A) and murine Myc-Cap prostate tumor cells (B).
Figure 7B:
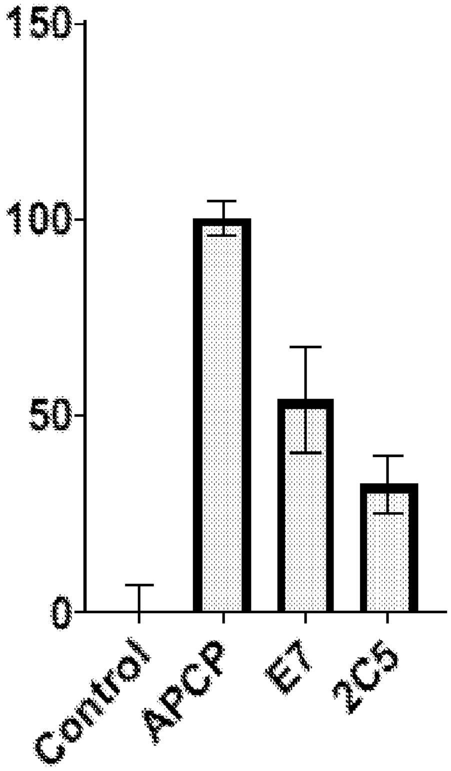

Experiments were conducted during development of embodiments herein to examine the ability of E7 or 2C5 to inhibit the enzymatic activity of CD73. A luminescence-based CD73 inhibitor screening assay was developed that utilizes measurement of degradation of extracellular AMP into adenosine by CD73 expression on tumor cells incubated with these mAb or APCP (a well-known small molecular enzymatic inhibitor of CD73; used as positive control) within one hour. E7 was capable of inhibiting the enzymatic activity of CD73 to a similar extent as 2C5 in both $CD73^+$ human (FIG. 7A) and mouse (FIG. 7B) prostate tumor cells, but less potent as compared to APCP.

Figure 8:
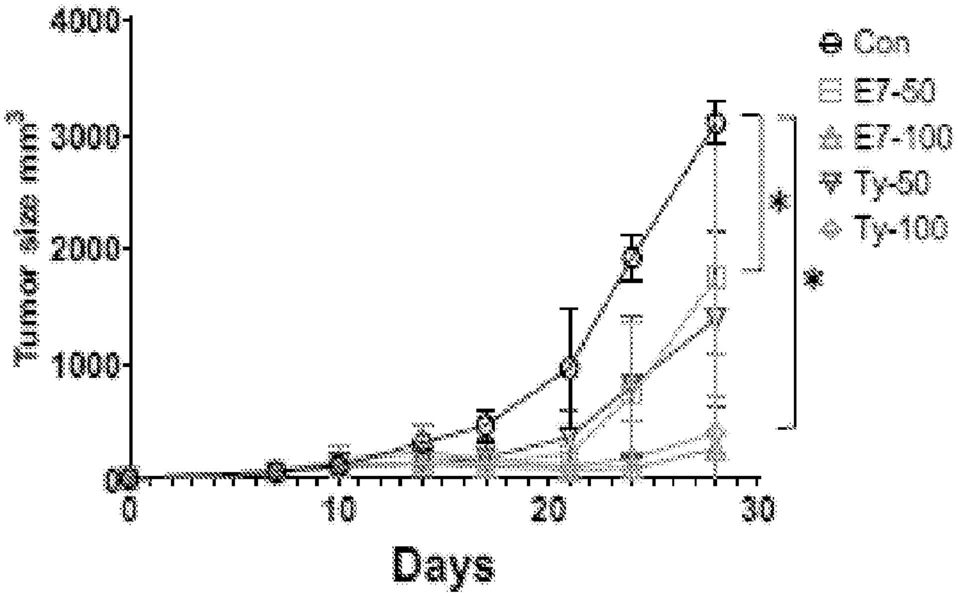
FIG. 8. E7 induces tumor regression. E0771 breast tumor-bearing C57BL/6 mice were treated with control IgG, E7 (50 ug or 100 ug per mouse, twice weekly) or TY-23 anti-CD73 antibody (50 ug or 100 ug per mouse, twice weekly) starting on day 7 for 4 times. Tumor size was measured every 3-4 days. Data are represented as mean±SEM (*p<0.05).

Experiments were conducted during development of embodiments herein to investigate the therapeutic potential of E7, C57BL/6 mice (5 mice per group) were s.c. injected with $CD73^+$ E0771 breast tumor cells. On day 7, mice were treated i.p. with control IgG (100 μg per mouse), E7 (50 or 100 μg per mouse), or TY-23 (a widely used mCD73 neutralizing mAb; 50 or 100 μg per mouse) twice weekly for total 4 times. Tumor size was measured every 3-4 days by caliper. Similar to TY-23, E7 was able to significantly inhibit tumor growth in a dose-dependent fashion (FIG. 8).

SEQUENCES

SEQ ID NO: 1-E7 Light Chain Variable Region Nucleic Acid Sequence
gatattgtgctgacgcaggctgcattctccagtccagtcactcttggaacgtcagcttccatctcctgcaggtctagtaagagtctcctgc
atagtgatggcttcacttatttgtattggtatctgcagaggccaggccagtctcctcagctcctgatatatcggatgtccaaccttgcctca
gcagtcccagacaggttcagtggcagtgggtcaggaactgatttcacactgagaatcagcagagtgggggctgaggatgtgggtgttt
attactgtgctcaaatgctagaattcccgtacacgttcggaggggggaccaagctggaaatcaaac SEQ ID NO: 2-E7 Light Chain Variable Region Amino Acid Sequence
DIVLTQAAFSSPVTLGTSASISCRSSKSLLHSDGFTYLYWYLQRPGQSPQLLIYRMSNL
ASAVPDRFSGSGSGTDFTLRISRVGAEDVGVYYCAQMLEFPYTFGGGTKLEIK SEQ ID NO: 3-E7 Heavy Chain Variable Region Nucleic Acid Sequence
gaggtgcagctgcaggagtctggacctgagctggtgaatcctggggcctcagtgaagatttcctgcaaagcttctggctacgctttcaa
tacgtactggataaactgggtgatgcagaggcctggaaagggtcttgaatggattggacggatttatcctggaggtggacatactaact
acaatgggaaattcaagggcaaggccatactgactgcagacagttcctccagtacagcctatatgcaactcagcagcctgacatctga
ggactctgcggtctacttctgtgcaagacccagtgatccctattactttgttatggactactggggtcaaggaacctcagtcaccgtctcc
gcag SEQ ID NO: 4-E7 Heavy Chain Variable Region Amino Acid Sequence
EVQLQESGPELVNPGASVKISCKASGYAFNTYWINWVMQRPGKGLEWIGRIYPGGG
HTNYNGKFKGKAILTADSSSSTAYMQLSSLTSEDSAVYFCARPSDPYYFVMDYWGQ
GTSVTVSA SEQ ID NO: 5-E7 Light Chain CDR1
KSLLHSDGFTY SEQ ID NO: 6-E7 Light Chain CDR2
RMS SEQ ID NO: 7-E7 Light Chain CDR3
AQMLEFPYT SEQ ID NO: 8-E7 Heavy Chain CDR1
GYAFNTYW -continued

| SEQUENCES |
| --- |

SEQ ID NO: 9-E7 Heavy Chain CDR2
IYPGGGHT

SEQ ID NO: 10-E7 Heavy Chain CDR3
ARPSDPYYFVMDY

SEQ ID NO: 11-Human CD73
MCPRAARAPATLLLALGAVLWPAAGAWELTILHTNDVHSRLEQTSEDSSKCVNASR
CMGGVARLFTKVQQIRRAEPNVLLLDAGDQYQGTIWFTVYKGAEVAHFMNALRYD
AMALGNHEFDNGVEGLIEPLLKEAKFPILSANIKAKGPLASQISGLYLPYKVLPVGDE
VVGIVGYTSKETPFLSNPGTNLVFEDEITALQPEVDKLKTLNVNKIIALGHSGFEMDK
LIAQKVRGVDVVVGGHSNTFLYTGNPPSKEVPAGKYPFIVTSDDGRKVPVVQAYAF
GKYLGYLKIEFDERGNVISSHGNPILLNSSIPEDPSIKADINKWRIKLDNYSTQELGKTI
VYLDGSSQSCRFRECNMGNLICDAMINNNLRHTDEMFWNHVSMCILNGGGIRSPIDE
RNNGTITWENLAAVLPFGGTFDLVQLKGSTLKKAFEHSVHRYGQSTGEFLQVGGIH
VVYDLSRKPGDRVVKLDVLCTKCRVPSYDPLKMDEVYKVILPNFLANGGDGFQMIK
DELLRHDSGDQDINVVSTYISKMKVIYPAVEGRIKFSTGSHCHGSFSLIFLSLWAVIFV
LYQ SEQ ID NO: 12-Mouse CD73
MRPAAAKVPKWLLLALSALLPQWPAASAWELTILHTNDVHSRLEQTSDDSTKCLNA
SLCVGGVARLFTKVQQIRKEEPNVLFLDAGDQYQGTIWFTVYKGLEVAHFMNILGY
DAMALGNHEFDNGVEGLIDPLLRNVKFPILSANIKARGPLAHQISGLFLPSKVLSVGG
EVVGIVGYTSKETPFLSNPGTNLVFEDEISALQPEVDKLKTLNVNKIIALGHSGFEMD
KLIAQKVRGVDIVVGGHSNTFLYTGNPPSKEVPAGKYPFIVTADDGRQVPVVQAYAF
GKYLGYLKVEFDDKGNVITSYGNPILLNSSIPEDATIKADINQWRIKLDNYSTQELGR
TIVYLDGSTQTCRFRECNMGNLICDAMINNNLRHPDEMFWNHVSMCIVNGGGIRSPI
DEKNNGTITWENLAAVLPFGGTFDLVQLKGSTLKKAFEHSVHRYGQSTGEFLQVGGI
HVVYDINRKPWNRVVQLEVLCTKCRVPIYEPLEMDKVYKVTLPSYLANGGDGFQMI
KDELLKHDSGDQDISVVSEYISKMKVVYPAVEGRIKFSAASHYQGSFPLVILSFWAMI
LILYQ

The invention claimed is:

1. A CD73 binding agent comprising a light chain variable region comprising complementarity determining region (CDR) 1, CDR2, and CDR3 having the amino acid sequences of SEQ ID NOs: 5, 6, and 7, respectively; and a heavy chain variable region comprising complementarity determining region (CDR) 1, CDR2, and CDR3 having the amino acid sequences of SEQ ID NOs: 8, 9, and 10, respectively.

2. The CD73 binding agent of claim 1, wherein the light chain variable region comprises 70% or greater sequence identity with SEQ ID NO: 2.

3. The CD73 binding agent of claim 1, wherein the heavy chain variable region comprises 70% or greater sequence identity with SEQ ID NO: 4.

4. The CD73 binding agent of claim 1, wherein the CD73 binding agent is an antibody or antibody fragment.

5. The CD73 binding agent of claim 1, wherein the CD73 binding agent is selected from a Fab, F (ab') 2, monospecific Fab2, monovalent antibody, scFv-Fc, and minibody.

6. The CD73 binding agent of claim 1, wherein the CD73 binding agent inhibits the activity of human CD73.

7. The CD73 binding agent of claim 1, wherein the CD73 binding agent mediates internalization of human CD73.

8. A pharmaceutical composition comprising the CD73 binding agent of claim 1, and a pharmaceutically acceptable carrier.

9. A nucleic acid encoding the CD73 binding agent of claim 1.

10. A vector or cell comprising the nucleic acid of claim 9.

11. A method of treating a cancer that expresses CD73 in a mammal, the method comprising administering an effective amount of the pharmaceutical composition of claim 8 to the mammal.

12. The method of claim 11, wherein the cancer is melanoma, renal cell carcinoma, lung cancer, bladder cancer, ovarian cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

13. The method of claim 11, wherein the mammal is a human.

14. The method of claim 11, further comprising co-administering one or more additional therapeutic agents.

* * * * *

SEQUENCE LISTING

<160> NUMBER OF SEQ ID NOS: 12

<210> SEQ ID NO 1
<211> LENGTH: 337
<212> TYPE: DNA
<213> ORGANISM: Mus musculus

<400> SEQUENCE: 1
gatattgtgc tgacgcaggc tgcattctcc agtccagtca ctcttggaac gtcagcttcc 60
atctcctgca ggtctagtaa gagtctcctg catagtgatg gcttcactta tttgtattgg 120
tatctgcaga ggccaggcca gtctcctcag ctcctgatat atcggatgtc caaccttgcc 180
tcagcagtcc cagacaggtt cagtggcagt gggtcaggaa ctgatttcac actgagaatc 240
agcagagtgg gggctgagga tgtgggtgtt tattactgtg ctcaaatgct agaattcccg 300
tacacgttcg gaggggggac caagctggaa atcaaac 337

<210> SEQ ID NO 2
<211> LENGTH: 112
<212> TYPE: PRT
<213> ORGANISM: Mus musculus

<400> SEQUENCE: 2

Asp Ile Val Leu Thr Gln Ala Ala Phe Ser Ser Pro Val Thr Leu Gly
1 5 10 15

Thr Ser Ala Ser Ile Ser Cys Arg Ser Ser Lys Ser Leu Leu His Ser
20 25 30

Asp Gly Phe Thr Tyr Leu Tyr Trp Tyr Leu Gln Arg Pro Gly Gln Ser
35 40 45

-continued

```
Pro Gln Leu Leu Ile Tyr Arg Met Ser Asn Leu Ala Ser Ala Val Pro
    50                  55                  60

Asp Arg Phe Ser Gly Ser Gly Ser Gly Thr Asp Phe Thr Leu Arg Ile
65                  70                  75                  80

Ser Arg Val Gly Ala Glu Asp Val Gly Val Tyr Tyr Cys Ala Gln Met
                85                  90                  95

Leu Glu Phe Pro Tyr Thr Phe Gly Gly Gly Thr Lys Leu Glu Ile Lys
            100                 105                 110


<210> SEQ ID NO 3
<211> LENGTH: 361
<212> TYPE: DNA
<213> ORGANISM: Mus musculus

<400> SEQUENCE: 3

gaggtgcagc tgcaggagtc tggacctgag ctggtgaatc ctggggcctc agtgaagatt      60

tcctgcaaag cttctggcta cgctttcaat acgtactgga taaactgggt gatgcagagg     120

cctggaaagg gtcttgaatg gattggacgg atttatcctg gaggtggaca tactaactac     180

aatgggaaat tcaagggcaa ggccatactg actgcagaca gttcctccag tacagcctat     240

atgcaactca gcagcctgac atctgaggac tctgcggtct acttctgtgc aagacccagt     300

gatccctatt actttgttat ggactactgg ggtcaaggaa cctcagtcac cgtctccgca     360

g                                                                     361


<210> SEQ ID NO 4
<211> LENGTH: 120
<212> TYPE: PRT
<213> ORGANISM: Mus musculus

<400> SEQUENCE: 4

Glu Val Gln Leu Gln Glu Ser Gly Pro Glu Leu Val Asn Pro Gly Ala
1               5                   10                  15

Ser Val Lys Ile Ser Cys Lys Ala Ser Gly Tyr Ala Phe Asn Thr Tyr
            20                  25                  30

Trp Ile Asn Trp Val Met Gln Arg Pro Gly Lys Gly Leu Glu Trp Ile
        35                  40                  45

Gly Arg Ile Tyr Pro Gly Gly Gly His Thr Asn Tyr Asn Gly Lys Phe
    50                  55                  60

Lys Gly Lys Ala Ile Leu Thr Ala Asp Ser Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Pro Ser Asp Pro Tyr Tyr Phe Val Met Asp Tyr Trp Gly Gln
            100                 105                 110

Gly Thr Ser Val Thr Val Ser Ala
        115                 120


<210> SEQ ID NO 5
<211> LENGTH: 11
<212> TYPE: PRT
<213> ORGANISM: Mus musculus

<400> SEQUENCE: 5

Lys Ser Leu Leu His Ser Asp Gly Phe Thr Tyr
1               5                   10


<210> SEQ ID NO 6
```

<211> LENGTH: 3
<212> TYPE: PRT
<213> ORGANISM: Mus musculus

<400> SEQUENCE: 6

Arg Met Ser
1

<210> SEQ ID NO 7
<211> LENGTH: 9
<212> TYPE: PRT
<213> ORGANISM: Mus musculus

<400> SEQUENCE: 7

Ala Gln Met Leu Glu Phe Pro Tyr Thr
1 5

<210> SEQ ID NO 8
<211> LENGTH: 8
<212> TYPE: PRT
<213> ORGANISM: Mus musculus

<400> SEQUENCE: 8

Gly Tyr Ala Phe Asn Thr Tyr Trp
1 5

<210> SEQ ID NO 9
<211> LENGTH: 8
<212> TYPE: PRT
<213> ORGANISM: Mus musculus

<400> SEQUENCE: 9

Ile Tyr Pro Gly Gly Gly His Thr
1 5

<210> SEQ ID NO 10
<211> LENGTH: 13
<212> TYPE: PRT
<213> ORGANISM: Mus musculus

<400> SEQUENCE: 10

Ala Arg Pro Ser Asp Pro Tyr Tyr Phe Val Met Asp Tyr
1 5 10

<210> SEQ ID NO 11
<211> LENGTH: 574
<212> TYPE: PRT
<213> ORGANISM: Homo sapiens

<400> SEQUENCE: 11

Met Cys Pro Arg Ala Ala Arg Ala Pro Ala Thr Leu Leu Leu Ala Leu
1 5 10 15

Gly Ala Val Leu Trp Pro Ala Ala Gly Ala Trp Glu Leu Thr Ile Leu
20 25 30

His Thr Asn Asp Val His Ser Arg Leu Glu Gln Thr Ser Glu Asp Ser
35 40 45

Ser Lys Cys Val Asn Ala Ser Arg Cys Met Gly Gly Val Ala Arg Leu
50 55 60

Phe Thr Lys Val Gln Gln Ile Arg Arg Ala Glu Pro Asn Val Leu Leu
65 70 75 80

Leu Asp Ala Gly Asp Gln Tyr Gln Gly Thr Ile Trp Phe Thr Val Tyr
85 90 95

-continued

```
Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
```

```
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570


<210> SEQ ID NO 12
<211> LENGTH: 576
<212> TYPE: PRT
<213> ORGANISM: Mus musculus

<400> SEQUENCE: 12

Met Arg Pro Ala Ala Ala Lys Val Pro Lys Trp Leu Leu Leu Ala Leu
1               5                   10                  15

Ser Ala Leu Leu Pro Gln Trp Pro Ala Ala Ser Ala Trp Glu Leu Thr
            20                  25                  30

Ile Leu His Thr Asn Asp Val His Ser Arg Leu Glu Gln Thr Ser Asp
        35                  40                  45

Asp Ser Thr Lys Cys Leu Asn Ala Ser Leu Cys Val Gly Gly Val Ala
    50                  55                  60

Arg Leu Phe Thr Lys Val Gln Gln Ile Arg Lys Glu Glu Pro Asn Val
65                  70                  75                  80

Leu Phe Leu Asp Ala Gly Asp Gln Tyr Gln Gly Thr Ile Trp Phe Thr
                85                  90                  95

Val Tyr Lys Gly Leu Glu Val Ala His Phe Met Asn Ile Leu Gly Tyr
            100                 105                 110

Asp Ala Met Ala Leu Gly Asn His Glu Phe Asp Asn Gly Val Glu Gly
        115                 120                 125

Leu Ile Asp Pro Leu Leu Arg Asn Val Lys Phe Pro Ile Leu Ser Ala
    130                 135                 140

Asn Ile Lys Ala Arg Gly Pro Leu Ala His Gln Ile Ser Gly Leu Phe
145                 150                 155                 160

Leu Pro Ser Lys Val Leu Ser Val Gly Gly Glu Val Val Gly Ile Val
                165                 170                 175

Gly Tyr Thr Ser Lys Glu Thr Pro Phe Leu Ser Asn Pro Gly Thr Asn
            180                 185                 190

Leu Val Phe Glu Asp Glu Ile Ser Ala Leu Gln Pro Glu Val Asp Lys
        195                 200                 205

Leu Lys Thr Leu Asn Val Asn Lys Ile Ile Ala Leu Gly His Ser Gly
    210                 215                 220

Phe Glu Met Asp Lys Leu Ile Ala Gln Lys Val Arg Gly Val Asp Ile
225                 230                 235                 240

Val Val Gly Gly His Ser Asn Thr Phe Leu Tyr Thr Gly Asn Pro Pro
                245                 250                 255

Ser Lys Glu Val Pro Ala Gly Lys Tyr Pro Phe Ile Val Thr Ala Asp
            260                 265                 270

Asp Gly Arg Gln Val Pro Val Val Gln Ala Tyr Ala Phe Gly Lys Tyr
        275                 280                 285

Leu Gly Tyr Leu Lys Val Glu Phe Asp Asp Lys Gly Asn Val Ile Thr
    290                 295                 300

Ser Tyr Gly Asn Pro Ile Leu Leu Asn Ser Ser Ile Pro Glu Asp Ala
305                 310                 315                 320
```

-continued

```
Thr Ile Lys Ala Asp Ile Asn Gln Trp Arg Ile Lys Leu Asp Asn Tyr
                325                 330                 335

Ser Thr Gln Glu Leu Gly Arg Thr Ile Val Tyr Leu Asp Gly Ser Thr
            340                 345                 350

Gln Thr Cys Arg Phe Arg Glu Cys Asn Met Gly Asn Leu Ile Cys Asp
        355                 360                 365

Ala Met Ile Asn Asn Asn Leu Arg His Pro Asp Glu Met Phe Trp Asn
    370                 375                 380

His Val Ser Met Cys Ile Val Asn Gly Gly Gly Ile Arg Ser Pro Ile
385                 390                 395                 400

Asp Glu Lys Asn Asn Gly Thr Ile Thr Trp Glu Asn Leu Ala Ala Val
                405                 410                 415

Leu Pro Phe Gly Gly Thr Phe Asp Leu Val Gln Leu Lys Gly Ser Thr
            420                 425                 430

Leu Lys Lys Ala Phe Glu His Ser Val His Arg Tyr Gly Gln Ser Thr
        435                 440                 445

Gly Glu Phe Leu Gln Val Gly Gly Ile His Val Val Tyr Asp Ile Asn
    450                 455                 460

Arg Lys Pro Trp Asn Arg Val Val Gln Leu Glu Val Leu Cys Thr Lys
465                 470                 475                 480

Cys Arg Val Pro Ile Tyr Glu Pro Leu Glu Met Asp Lys Val Tyr Lys
                485                 490                 495

Val Thr Leu Pro Ser Tyr Leu Ala Asn Gly Gly Asp Gly Phe Gln Met
            500                 505                 510

Ile Lys Asp Glu Leu Leu Lys His Asp Ser Gly Asp Gln Asp Ile Ser
        515                 520                 525

Val Val Ser Glu Tyr Ile Ser Lys Met Lys Val Val Tyr Pro Ala Val
    530                 535                 540

Glu Gly Arg Ile Lys Phe Ser Ala Ala Ser His Tyr Gln Gly Ser Phe
545                 550                 555                 560

Pro Leu Val Ile Leu Ser Phe Trp Ala Met Ile Leu Ile Leu Tyr Gln
                565                 570                 575
```